United States Patent [19]
Petruzzi

[11] Patent Number: 4,655,219
[45] Date of Patent: Apr. 7, 1987

[54] MULTICOMPONENT FLEXIBLE GRASPING DEVICE

[75] Inventor: Claude E. Petruzzi, Bronxville, N.Y.

[73] Assignee: American Hospital Supply Corporation, Evanston, Ill.

[21] Appl. No.: 880,333

[22] Filed: Jun. 24, 1986

Related U.S. Application Data

[63] Continuation of Ser. No. 516,225, Jul. 22, 1983, abandoned.

[51] Int. Cl.$^4$ ................................................ A61B 1/06
[52] U.S. Cl. ........................................ 128/321; 128/6
[58] Field of Search ............... 128/321, 6, 303 R, 322, 128/4, 5

[56] References Cited

U.S. PATENT DOCUMENTS

| 3,529,633 | 9/1970 | Vaillancourt | 138/118 |
| 3,934,589 | 1/1976 | Zimmer | 128/321 |
| 4,003,380 | 1/1977 | Wien | 128/321 |
| 4,085,743 | 4/1978 | Yoon | 128/6 |
| 4,174,715 | 11/1979 | Hasson | 128/321 |
| 4,467,802 | 8/1984 | Maslanka | 128/321 |

Primary Examiner—C. Fred Rosenbaum
Assistant Examiner—Gene B. Kartchner
Attorney, Agent, or Firm—Perman & Green

[57] ABSTRACT

A unique manipulative/grasping assembly adapted for use in conjunction with endoscopic instruments in disclosed herein. This assembly comprises an elongated tool having an elongated shaft with resilient, flexible fingers on the distal end thereof. These fingers can be biased in a spaced apart relationship. The tool of the shaft is housed within the channel of a first tubular sheath, and a second such tubular member concentrically surrounds the first tubular member, although somewhat shorter in length than the first tubular member. In the preferred embodiments of this invention, the proximal end of the tool and the second tubular member are cofixated to a stationary platform conveniently located along with the other controls of the endoscope. The proximal end of the inner tubular sheath is attached to a moveable, or sliding platform within this common control mechanism. In the operation of this assembly, the inner tubular sheath is extended or retracted along the shaft of the tool thereby enabling engagement of an object by the flexible fingers of the shaft without any axial motion of the tool or recession of the fingers of the tool from the object during the grasping procedure.

6 Claims, 14 Drawing Figures

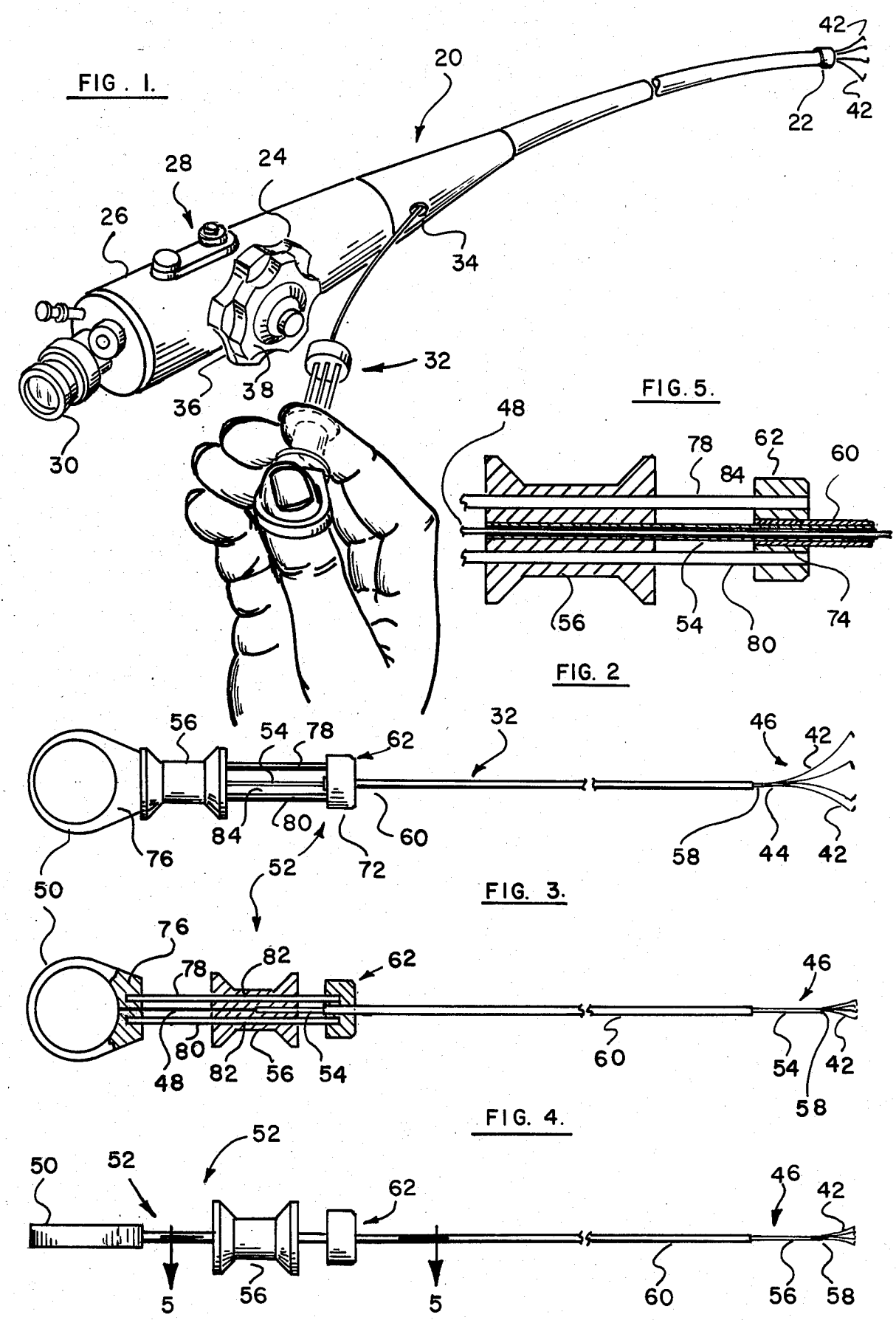

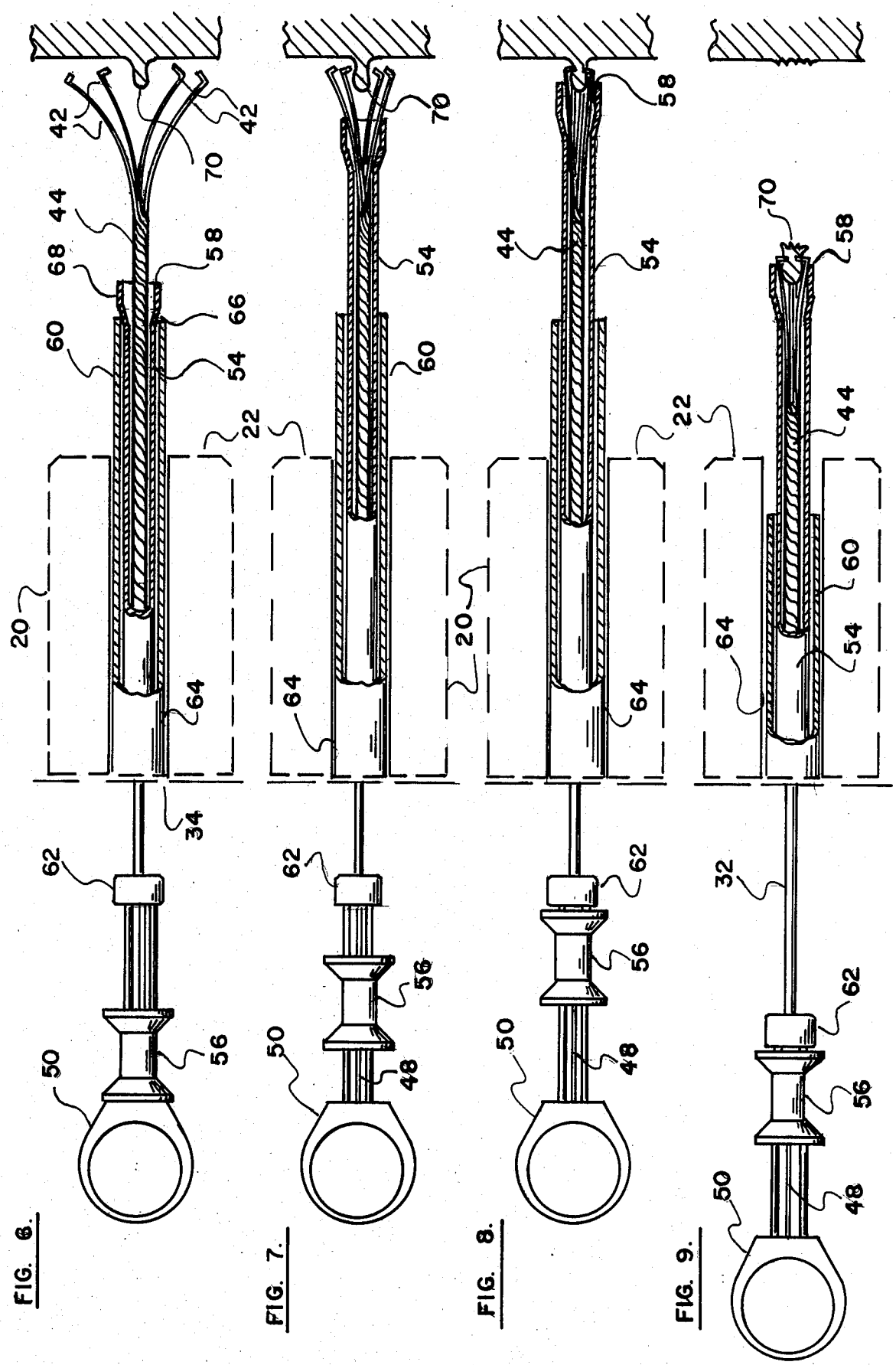

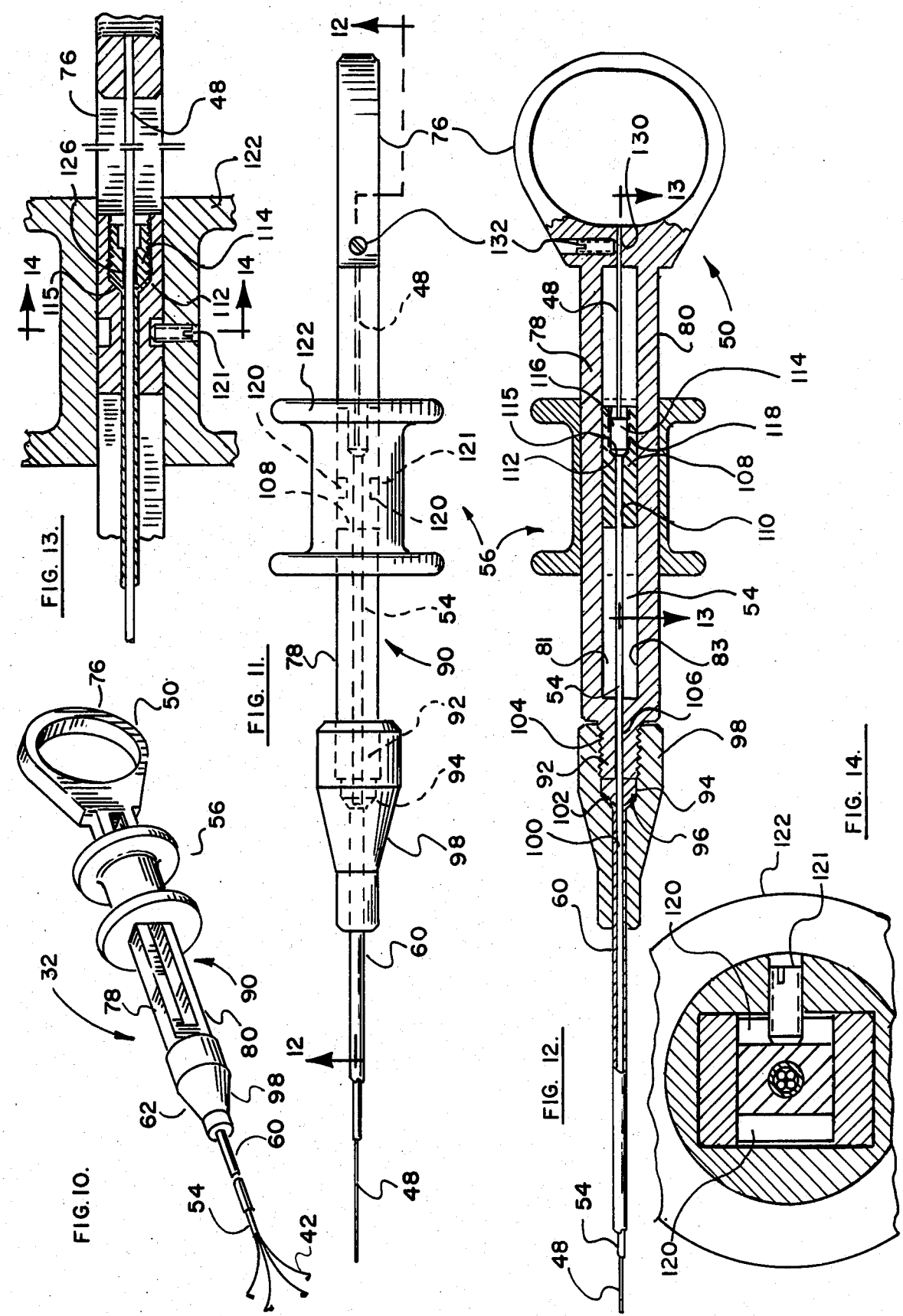

MULTICOMPONENT FLEXIBLE GRASPING DEVICE

This is a continuation of co-pending application Ser. No. 516,225 filed on July 22, 1983, now abandoned.

BACKGROUND OF THE INVENTION

Field of the Invention

This invention relates to an apparatus and to a method. More specifically, this invention concerns itself with a unique forceps-like assembly adapted for use in conjunction with endoscopic instruments; and a method for the grasping/manipulation of objects within a bodily cavity by such endoscopic instruments.

Description of the Prior Art

The advent of flexible endoscopic instruments has made possible the invasive, non-surgical examination of the remote areas of the gastrointestinal tract. In addition, various surgical and manipulative accessories have also been developed for use in conjunction with such endoscopic instruments to perform minor surgical procedures and/or the removal of obstructive deposits from remote areas now made accessible by such endoscopic instruments. These accessories have, thus, expanded the versatility of such instruments and provide the physician with an alternative to the more traditional, and decidedly more traumatic, surgical procedures.

One common accessory which has greatly enhanced the utility of endoscopic instruments, is forceps. Typically, this accessory can consist of an elongated shaft having a plurality of resilient fingers disposed on one end thereof. These fingers can be manipulated or alternatively are biased in a spaced apart relationship. The opposite end of the shaft is fitted with an actuator mechanism which enables both extention and operation of such fingers in the field of operative interest. This accessory generally consists of one other component, namely a tubular element or sheath, through which the elongated forceps shaft can be extended or withdrawn. This accessory is generally initially prepositioned within the channel provided therefor in an endoscopic instrument, the endoscopic instrument inserted by the physician into the patient and the distal end of the instrument manipulated so as to provide the physician with visual access to the field of operative interest. The physician may thereafter extend/advance the forceps from its channel within the endoscope so as to position the fingers thereof around an object to effect either its manipulation or eventual grasping and removal. The operation of the forceps of the type described hereinabove is traditionally dependent upon axial motion of the forceps relative to the endoscope to achieve opening and closing the grasp of these fingers. As is readily appreciated, where the forceps are used in conjunction with relatively long endoscopic instruments, typically on the order of two to three feet, the physician is required to initially position the forceps in the manner described above and thereafter further advance the endoscopic instrument into the patient in the direction of the tissue/deposit so as to maintain the fingers of the forceps in a stationary position relative to the object which is to be grasped. As is evident from the foregoing description, the axial movement of the forceps assembly into the endoscope to effect closure thereof will cause the forceps to recede out of range of grasping distance of the object.

U.S. Pat. Nos. 4,003,380; 4,174,715; 4,085,743 all disclose various accessory tools suitable for use in endoscopic instruments. Each of the devices disclosed by these patents reveals a forceps assembly comprising of an elongated shaft and two concentrically arranged tubular members. In each of the accessory tools, an elongated shaft (either disposed within a tubular member and the manipulative/operative components of the tool) is extended from the tube or withdrawn into it as a means of manipulating the functional implement of each such tool. In virtually all instances of operation of the devices described in these patents, compensatory axial motion of the endoscope is required to maintain the functional implement of the tool stationary relative to the site of operative interest.

As is evident from the foregoing discussion, all the prior art devices in which a manipulative instrument is used and which requires extention and retraction of the grasping element into a tubular member for the articulation thereof, are limited in their utility, and often times difficult to operate, because such extention and retraction results in a recession of the tool from the site of operative interest. This recession of the tool generally places the object out of range of the grasping elements of the tool. Absent compensatory movement of the endoscope shaft, the tool cannot remain stationary, vis-a-vis, the field of operative interest. Where such accessories are used in endoscopic instruments of substantial length, the achievement of such compensatory motion is greatly complicated. Thus, there is a continuing need for an accessory forceps which can be operated essentially independent of axial movement of the endoscopic shaft and which is otherwise compatible with the existing operation of the endoscope.

OBJECTS OF THE INVENTION

Accordingly, it is the object of this invention to remedy the above as well as related deficiencies in the prior art.

More specifically, it is the principal object of this invention to provide an accessory forceps for use in conventional endoscopic instruments which is capable of manipulation/grasping of an object of interest within an operative field independent of relative axial motion of the endoscope.

It is another object of this inventon to provide an improved accessory forceps for an endoscopic instrument wherein the manipulative grasping elements on such accessory are opened and closed without movement of the shaft to which such elements are attached.

It is yet another object of this invention to provide an improved accessory forceps for use in endoscopic instruments in which the actuation and/or manipulation of the forceps is perfected through a control mechanism which operates independent of relative axial movement of the endoscopic instrument.

Yet another object of this invention is to provide an improved accessory forceps for use in endoscopic instruments in which the actuation and/or manipulation of the forceps is effected without any relative movement of the endoscope, vis-a-vis, the field of operative interest.

Additional objects of this invention include a method for use of this improved forceps accessory in conjunction with an endoscopic instrument and the removal of tissue specimens with such improved accessory.

SUMMARY OF THE INVENTION INCLUDING PREFERRED EMBODIMENTS

The above and related objects are achieved by providing an improved accessory tool for use in conjunction with endoscopic instruments. This improved accessory can comprise a forceps-like element located on the distal end of an elongated shaft which is actuated by the releasing of confinement of the grasping fingers of such element through the withdrawal of a tubular sheath which envelops such fingers. Upon proper positioning of the endoscope by the physician, the tool assembly is extended from its channel within the endoscope into the field of operative interest. Such extension of the distal end of the forceps from the channel results in release of constraint upon the fingers of the forceps which are biased in spaced-apart relationship to one another. The physician can thereafter position the forceps to engage the tissue specimen or obstructive deposit. Once positioned in range of the tissue specimen or obstructive deposit, the forceps can then grasp/manipulate such specimen or deposit by simply extending the tubular sheath along the shaft of the instrument in the direction of the tissue deposit. This extension of the tubular sheath is effected without any axial movement of the endoscope relative to the field of operative interest. The operation of this accessory in the above manner is critically dependent upon the ability to advance and retract the tubular sheath without relative axial movement of the endoscope. This type of forceps activation system greatly simplifies manipulation of the instrument by the physician and permits more precise control over the forceps itself.

In the preferred embodiments of this invention, the forceps-like instrument is affixed to the distal end of an elongated shaft which in turn resides within the channel of a tubular sheath. This tubular sheath is further coaxially enveloped by a second tubular member or liner which is somewhat shorter in length than the tubular sheath. The overall dimensions of this three component accessory are precisely adapted for use in endoscopic instruments of the type commonly used by physicians in both examination and in non-evasive surgical procedures. The accessory assembly of the type described hereinabove is adapted for insertion within a forceps channel of existing endoscopic instrument. Upon location of the field of operative interest by the physician, the entire assembly is sufficiently extended from the distal end of the endoscopic shaft to position the distal end of the accessory in close proximity to the tissue speciment or obstructive deposit.

The tubular sheath enveloping the shaft of the tool is then withdrawn through the control mechanism thereby expanding the fingers of forceps-like element on the distal end of the shaft in a space apart relation relative to the tissue or obstructive deposit. The endoscope then is advanced to position the fingers of forceps in range of grasping of the tissue sample or obstructive deposit. Subsequent to such positioning, the tubular member surrounding the shaft is advanced/extended so as to restrict the spread apart fingers at the end of the shaft to effect a grasping of the tissue/deposit. This grasping of the tissue/deposit is achieved without any relative movement of the endoscope.

BRIEF DESCRIPTION OF THE DRAWINGS

FIG. 1 is a perspective view of an endoscopic instrument equipped with the forceps-like assembly of this invention;

FIG. 2 is a side plan view of the forceps-like assembly of this invention wherein the grasping manipulative elements on the distal end are shown spread-apart;

FIG. 3 is a side plan view in partial section of the forceps-like assembly shown in FIG. 2;

FIG. 4 is a top plan view of the forceps-like assembly shown in FIG. 2;

FIG. 5 is an enlarged section view along the line 5—5 in FIG. 4;

FIGS. 6, 7, 8 and 9 are side plan views in partial cross-section of the instrument shown in FIG. 1, FIGS. 6–9 depicted the forceps-like assembly in progressive stages of operation relative to a tissue specimen;

FIG. 10 is a perspective view of another embodiment of the forceps-like assembly of the invention;

FIG. 11 is a broken top plan view of the assembly of FIG. 10;

FIG. 12 is a broken side view of the assembly of FIG. 10;

FIG. 13 is an enlarged view in partial cross-section of the assembly of FIG. 10 taken along the line 13—13 in FIG. 12; and FIG. 14 is an enlarged sectional view of the assembly of FIG. 10 taken along the line 14—14 in FIG. 13.

DESCRIPTION OF THE INVENTION INCLUDING PREFERRED EMBODIMENTS

With reference to FIG. 1, an endoscope 20 is shown whose distal end 22 may be maneuvered and deflected in various positions under control by a deflection mechanism 24 located and mounted to the head 26 at the proximal end 28 of the endoscope 20. Endoscope 20 is provided with suitable channels to accommodate an image carrier fiber optic bundle and a light carrier fiber optic bundle so as to permit observation of tissues or other objects through an eye piece 30 and to enable coordination of manipulative procedures with instrument 32 involving certain accessories (i.e., forceps or electrodes) shown applied through a proximal port 34.

When in use, the endoscope operator observes an internal body cavity through an eye piece 30 while holding head 26 in his left hand (as illustrated in U.S. Pat. No. 4,207,873) with his fingers in contact with deflection control wheels 36 and 38 of deflection mechanism 24.

The accessory 32 is of a type which incorporates at its distal end 40 a plurality of fingers 42 that are spring biased apart. In the embodiment of FIG. 1, the accessory 32 is a forceps with which an object may be grasped and/or manipulated.

As illustrated in FIGS. 2–9, the accessory 32, incorporates a tool 44 having, at distal end 46 of accessory 32, flexible grasping arms 42 connected to an elongated shaft 48. The shaft 48 is connected to a holder 50 located at the proximal end 52 of accessory 32. Tool 48 is enclosed by a tubular sheath 54 which is connected at proximal end 52 to a slide 56 movably mounted to holder 50. Hence, movement of slide 56 between the proximal and distal ends of holder 50, causes tubular sheath 54 to move relative to and over the flexible arms 42 as illustrated by FIGS. 2–4. With the slide 56 in the rear position shown in FIG. 2, the tubular sheath's distal end 58 is drawn away from the arms 42 which are unrestrained and thus flex to their maximum biased position. As slide 56 is moved forwardly, the distal end 58 of tubular sheath 54 moves over the arms 42, thus forcing them to close.

Accessory 32 overcomes the cumbersome nature of prior art forceps by the inclusion of an outer liner 60 in the form of an elongated tube. Liner 60 encloses most of tubular sheath 54 and is affixed to holder 50 at the latter's distal end 62. Liner 60 serves to maintain a working position of the accessory 32 in an endoscope channel while allowing tubular 54 to be easily moved back and forth under control by slide 56 to correspondingly control the opening and closure of arms 42.

Liner 60 and tubular sheath 54 preferably interfit with each other in such manner that inner tube 54 may easily slide, with little backlash, within the liner 60 while the latter conveniently maintains a desired working position. One technique for maintaining the liner 60, and thus the accessory 32, at a desired working position relies upon the frictional force between the liner 60 and the wall of the endoscope channel through which the accessory 32 is passed. The length of the liner 60 may be so selected that accessory 32 develops a frictional force with the wall of the endoscope channel sufficient to maintain a working position in the channel under normal working conditions of the endoscope 20 and accessory 32. Another technique for generating such frictional endoscopic portion may utilize a restriction device (not shown) placed, for example, at port 34 (see FIG. 1) leading to the endoscope channel. Such restriction device would have a through bore sized, or formed with a frictional wall material, to develop sufficient frictional force with liner 60 without unduly affecting the movement of the tubular sheath 54.

In the embodiment illustrated, both the liner 60 and the tubular sheath 54 are each made of polytetrafluoroethylene material (i.e., Teflon, a product of E. I. du Pont de Nemours, Wilmington, Del., USA) and have cross-sectional dimensions so that, in case of tubular cylindrical construction, the inner diameter of liner 60 is greater than the outer diameter of tubular sheath 54 in the range from about 0.003 to about 0.007 inches, with a preferred difference of about 0.005 inches. With such clearance between the liner 60 and tubular sheath 54, and the use of low friction materials, the sheath 54 can be easily moved back and forth with little longitudinal backlash.

FIGS. 6-9 illustrate the distal end 46 of accessory 32 with greater detail inside a channel 64 of endoscope 20. Tubular sheath 54 is provided with a radially enlrged distal end 58 having a flared segment 66 and a straight cylindrical segment 68. This enables arms 42, when the slide 56 is at the distal end of its stroke, to recede inside tubular sheath 54 and also reduce stresses imposed on the distal end 58 when an object, such as 70, is grasped and removed as shown in FIG. 9.

In the embodiment as shown, the tubular sheath 54 may have a length of the order of about 19 inches and the liner a length of about 17 inches and interfit in a manner as described. Tool 44 includes four forceps arms 42 that are spring biased in spread-apart relation to each other as shown in FIGS. 2 and 6 and extend from elongated shaft 48. The shaft is preferably made from a plurality of twisted steel strands with the tips of arms 42 bent inwardly to form claws for grasping an object such as 70 (see FIGS. 6-9).

As shown in FIGS. 2-5, the holder 50 includes an anterior bushing 72 at its distal end 62 having a central axial bore 74. Liner 60 is secured to bushing 72. The tubular sheath 54 and shaft 48 extend rearwardly through bushing passage 74 with the proximal end of shaft 48 secured to the proximal ring shaped portion 76 of holder 50. The ring portion 76 is sized to laterally receive the thumb as shown in FIG. 1. The proximal end of tubular sheath 54 is secured to slide 56.

Holder 50 further includes two elongated guide rails 78, 80 which connect the anterior bushing 62 with the ring portion 76 of holder 50. The guide rails 76, 80 extend through slightly larger bores 82 in slide 56. Slide 56 is mounted for reciprocal sliding movement in the space 84 between ring portion 76 and bushing 62.

Referring to FIGS. 1 and 6-9, the manner of using the accessory 32 in accordance with the present invention commences by inserting the distal end 22 of the endoscope 20 into a body cavity to, for example, first locate and then remove a stone or apply a bipolar treatment of tissue in medical procedures involving, for example, urological, hepatoscopy, gastroenterology or bronchiogenic investigations. The accessory 32 is inserted through endoscope channel 64 until the distal end of the instrument protrudes from the distal end 22 of endoscope 20. Prior to and during inserting of the accessory 32 through the endoscope channel 64, the slide 56 is moved to its most distal position to thereby close the arms 42 and thus enable the instrument to pass through channel 64.

When the physician using the endoscope observes an object 70 through the eye piece 30, he or she manipulates the endoscope 20 and accessory 32 until the arms 42 are in a position to grasp object 70. The physician uses the left hand (not shown) to support the endoscope body 26 and operate the control wheels 36, 38 to move the distal end 22. The right hand is used to slide accessory 32 longitudinally along endoscope channel 64 to a working position as shown in FIG. 6.

Once the forceps are poised to grasp the object 70 as shown in FIG. 6, the frictional restraining force between the liner 60 and the interior wall of the endoscope channel 64 is sufficient to maintain the longitudinal working position of the accessory 32 while arms 42 are actuated to close by moving the slide 56 forwardly. This action of the slide advances tubular sheath 54 longitudinally inside liner 64, but since the frictional force between the tubular sheath 54 and liner 60 is less than the frictional force between the outer surface of liner 60 and the endoscope, the longitudinal working position of the instrument is maintained as shown in FIGS. 7 and 8. Once the object 70 has been grasped, accessory 32 is withdrawn from channel 64 to remove the object.

FIGS. 10-14 illustrate a preferred form for accessory 32 relating to the techniques for affixing the proximal ends of the tool 44, the tubular sheath 54 and liner 60 to holder 50 shown in detail. Holder 50 is formed with a ring shaped proximal end 76 affixed to a rectangular cross-sectional mid-segment 90 split into guide rods 78', 80' having flat facing slide surfaces. The distal end 62 of holder 50 is formed with an externally threaded segment 92 terminating in a conically tapered end 94 sized to snugly fit against a correspondingly shaped proximal flared end 96 of liner 60.

A clamp 98 having a through bore 100 sized to snugly receive the outside diameter of the liner 60 has a conical clamping surface 102 that complements surface 94. Clamp 98 has a threaded bore 104 that meshes with the threaded segment 92 to firmly press and affix the liner end 96 to holder 50'.

Segment 92 has a bore 106 sized to freely receive the tubular sheath 54 which is affixed to a slide connector 108 sized to fit, with slight clearance sufficient to slidingly move, between the flat facing surfaces 81, 83 of guide rods 78', 80'. Slide connector 108 has a through bore 110 which at its distal end is sized to snugly receive the tubular sheath 54. At the other proximal end bore 110 has a conical tapered surface 112 against which a correspondingly flared proximal end of the tubular sheath 54 is pressed by a clamp 114 having a mating end surface 115 and an externally threaded surface 116 to engage a correspondingly threaded bore 118. Clamp 114 thus affixes the tubular sheath 54 to slide 56' in a manner similar to clamp 92.

Slide connector 108 is provided with a pair of laterally facing slots 120, 120' each of which may receive a set screw 121 enabling an outer slide block 122 to be affixed to connector 108 with set screws 121.

Clamp 114 has a through bore 126 sized to freely receive the shaft 48 of tool 44. The shaft 48 extends through bore 126 to connect to ring end 76 by passing the tool shaft 48 thorugh a bore 130 and clamping the shaft 48 against a wall of bore 130 with a set screw 132.

The slide block 122 is provided with a rectangular shaped through bore 134 sized to snugly enclose midsegment 90 of holder 50 while yet permitting sliding movement between ring shaped end 76 and clamp 98. With accessory 32 as shown in FIGS. 10–14, a precise and delicate control over the opening and closure of tool arms 42 is obtained.

Having thus explained several forms of the invention, its advantages can be appreciated. A highly convenient and facile control over the instrument is obtained, while enabling the physician to maintain concentration on his targeting of the instrument on the tissue area to be grasped/manipulated from the distal end of an endoscope. Variations from the described forms can be made without departing from the scope of the invention.

What is claimed is:

1. A forceps-like accessory compatible for use in conjunction with an endoscopic instrument, said forceps-like accessory comprising:
   (a) an elongated shaft, said shaft being equipped on its distal end with a plurality of resilient finger-like appendages which are biased in spaced apart relation from one another;
   (b) a tubular sheath arranged about said elongated shaft for housing and guiding said elongated shaft of said accessory and its finger-like appendages during the relative movement thereof;
   (c) tubular means arranged about said sheath for engaging the forceps-like accessory to an accessory channel of said endoscopic instrument so as to restrain movement of said tubular means relative to said endoscopic instrument during movement of the tubular sheath of said accessory within the tubular means; and
   (d) control means for supporting said shaft and said tubular means so that there is essentially no longitudinal relative movement therebetween and for supporting said tubular sheath for reciprocal longitudinal movement in opposing directions relative to said tubular means and said shaft;
   whereby said sheath is operative to close or space apart said finger-like appendages without longitudinally moving said shaft by said reciprocal movement in said respective opposing direction.

2. The forceps-like accessory according to claim 1, having three (3) resilient forceps-like appendages.

3. The forceps-like accessory according to claim 1 wherein said shaft and tubular sheath are flexible to permit use of the tool in a channel of a flexible endoscope.

4. The forceps-like accessory according to claim 1, wherein said tubular means and said tubular sheath are formed of polytetrafluoroethylene material.

5. The forceps-like accessory according to claim 1, wherein said control means includes a holder having a proximal end and a distal end, said proximal end being shaped to receive a thumb, with said holder being affixed to the proximal ends of the tubular means and the shaft of the tool to maintain the latter in fixed spatial relationship to each other.

6. The forceps-like accessory according to claim 5 wherein said control means further include:
   guide means connecting the distal end of the holder to its proximal end;
   slide means mounted to slide over the guide means between the proximal and distal ends of the holder, said slide means being shaped to be finger actuated when a thumb is operatively placed in the holder;
   the proximal end of the tubular means being affixed to the distal end of the holder, and the proximal end of the shaft of the accessory being affixed to the proximal end of the holder; and
   with the proximal end of said sheath being connected to the slide means so that finger actuated movement thereof relative to the holder causes a corresponding motion of the sheath for actuation of said finger-like appendage.

* * * * *